United States Patent [19]

Evers

[11] Patent Number: Plant 7,665

[45] Date of Patent: Oct. 1, 1991

[54] ROSE PLANT TANELORAK

[75] Inventor: Hans Evers, Uetersen, Fed. Rep. of Germany

[73] Assignee: Bear Creek Gardens, Inc., Medford, Oreg.

[21] Appl. No.: 531,888

[22] Filed: Jun. 1, 1990

[51] Int. Cl.[5] ..... A01H 5/00

[52] U.S. Cl. ..... Plt./21

[58] Field of Search ..... Plt./20, 21

*Primary Examiner*—James R. Feyrer

*Attorney, Agent, or Firm*—Klarquist, Sparkman, Campbell, Leigh & Whinston

[57] ABSTRACT

A hybrid tea class rose having medium sized pointed buds, nearly black in color, large (up to 12 cm in diameter) open bloom of velvety red, very good fragrance, very long, strong stems with few side buds and big thorns, and resistant to blackspot and rust at Somis, Calif.

1 Drawing Sheet

This present invention relates to a new and distinct variety of rose plant of the hybrid tea class which was originated by me by crossing two unnamed seedlings.

The primary objective of this breeding was to produce a new rose variety having a very noble dark red color and good fragrance, and being very resistant to mildew and blackspot. The objective was substantially achieved along with other desirable improvements as evidenced by the following unique combination of characteristics which are outstanding in the new variety and which distinguish it from its parents, as well as from all other varieties of which I am aware:

1. Medium sized pointed buds, nearly black in color.
2. Large (up to 12 cm in diameter) open bloom of velvety red.
3. Very good fragrance.
4. Very long, strong stems with few side buds and big thorns.
5. Resistant to blackspot and rust at Somis, Calif.

Asexual reproduction of this new variety by budding, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart, except where ordinary dictionary significance of color is indicated.

Parentage:

*Seed parent.*—An unnamed seedling.

*Pollen parent.*—An unnamed seedling.

Classification:

*Botanical.*—*Rosa hybrida.*

*Commercial.*—Hybrid tea.

FLOWER

Observations made from specimens grown in a greenhouse environment in Somis, Calif., in Feb., 1990.

Blooming habit: Continuous.

Bud:

*Size.*—1½ to 2 inches when the petals start to unfurl.

*Form.*—Long, pointed ovoid.

*Color.*—When sepals first divide: Grey purple 187A. When half blown, the upper sides of the petals are: Red Group 45A with outer petals Red Group 46A; and the lower sides of the petals are: Red Group 46A.

*Sepals.*—Color: Green Group 138A. Surface texture: Covered in fine hairs. There are three heavily appendaged sepals. There are two unappendaged sepals with hairy edges.

*Receptacle.*—Color: Green Group 137C. Shape: Funnel. Size: Medium to small, ¼ inch wide. Surface: Smooth.

*Peduncle.*—Length: Medium, 3 inches long. Surface: Prickly. Color: Medium green. Strength: Stiff, erect.

Bloom:

*Size.*—Large. Average open size is 5 inches.

*Borne.*—Singly.

*Stems.*—Long, average of 26 inches.

*Form.*—When first open: High centered. Permanence: Outer petals curl back, quill fashion.

*Petalage.*—Number of petals under normal condition: 25 to 30.

*Color.*—The upper side of the petals is: Red Group 45A. The reverse side of the petals is: Red Group 46A. The base of petals is: Small yellow half moon at the point of attachment. The major color on the upper side is: Red Group 46A.

*Variegations.*—None.

*Discoloration.*—The general tonality at the end of the first day: None. At the end of the third day: None.

*Fragrance.*—Strong.

Petals:

*Texture.*—Thick.

*Shape.*—Deltoid.

*Form.*—Tips slightly recurved, edges slightly quilled.

*Arrangement.*—Imbricated. Petaloids in the center: Few.

*Persistence.*—Drop off cleanly.

*Lastingness.*—On the plant: Long, 5 to 7 days. As a cut flower: Long, 7 to 8 days.

Reproductive parts:

*Anthers.*—Size: Large. Quantity: Many. Color: Yellow. Arrangement: Regular around styles, mixed with occasional petaloids.

*Filaments.*—Color: Reddish brown.

*Pollen.*—Color: Lemon yellow.

*Styles.*—Color: Reddish and covered in fine white hairs.

*Stigmas.*—Color: Greenish white.

Form: Bush.

Growth: Very vigorous, upright, branching.

Foliage:

*Number of leaflets on normal mid-stem leaves.*—5, with occasional 7.

*Size.*—Large, 6 inches long.

*Quantity.*—Sparse.

*Color.*—New foliage: Reddish. Old foliage: Matte green.

Leaflets:

*Shape.*—Oval.

*Texture.*—Upper side: Smooth.

*Edge.*—Serrated.

*Serration.*—Single, small.

*Petiole rachis.*—Color: Green.

*Petiole underside.*—Rough, with prickles.

*Stipules.*—Medium, bearded, ½ to ¾ inch long.

*Disease resistance.*—Susceptible to mildew, but resistant to blackspot and rust, under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Many. On laterals from main canes: Many.

*Form.*—Hooked downward, ¼ inch long.

*Color when young.*—Red.

Small prickles:

*Quantity.*—On main stalks: Many. On laterals: Many.

*Color.*—Green.

I claim:

1. A new and distinct variety of rose plant of the hybrid tea class, substantially as herein shown and described, characterized particularly as to novelty by the unique combination of its medium sized pointed buds, nearly black in color; its large (12 cm), open bloom of velvety red; very good fragrance; very long, strong stems with few side buds and big thorns; and its resistance to blackspot and rust.

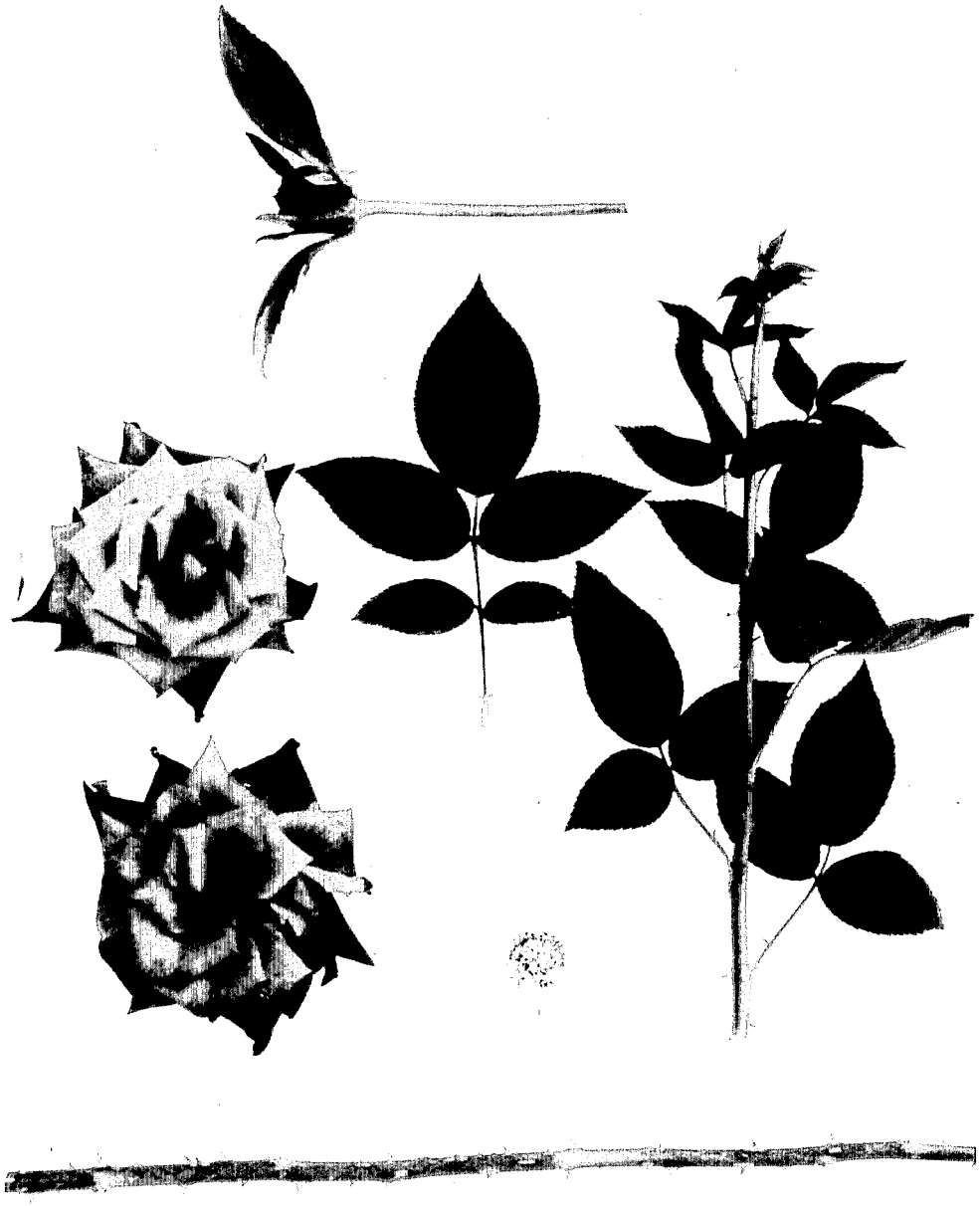

* * * * *